United States Patent
Ghelfi et al.

(10) Patent No.: US 8,143,443 B2
(45) Date of Patent: Mar. 27, 2012

(54) PROCESS FOR PREPARING GABAPENTIN

(75) Inventors: Franco Ghelfi, Modena (IT); Livius Cotarca, Cervignano del Friuli (IT); Fabrizio Roncaglia, Modena (IT); Roberto Giovanetti, Schio (IT); Andrea Nicoli, Vicenza (IT)

(73) Assignee: ZaCh System S.p.A., Bresso (IT)

( * ) Notice: Subject to any disclaimer, the term of this patent is extended or adjusted under 35 U.S.C. 154(b) by 461 days.

(21) Appl. No.: 12/305,674

(22) PCT Filed: Jun. 29, 2007

(86) PCT No.: PCT/IB2007/001977
§ 371 (c)(1), (2), (4) Date: Dec. 19, 2008

(87) PCT Pub. No.: WO2008/004115
PCT Pub. Date: Jan. 10, 2008

(65) Prior Publication Data
US 2010/0029983 A1 Feb. 4, 2010

(30) Foreign Application Priority Data
Jun. 30, 2006 (EP) .................................. 06116483

(51) Int. Cl.
*C07C 229/00* (2006.01)
(52) U.S. Cl. ...................................................... 562/507
(58) Field of Classification Search ................. None
See application file for complete search history.

(56) References Cited

U.S. PATENT DOCUMENTS

| 4,515,960 A | 5/1985 | Teetz |
| 5,136,091 A | 8/1992 | Mettler et al. |

OTHER PUBLICATIONS

Aldrich, Handbook of Fine Chemicals and Laboratory Equipment, 2002, Milwaukee, WI, p. 298.*

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

A process for preparing gabapentin of formula 1, which comprises Formula (I) converting 1-allyl-cyclohexanecarboxaldehyde into 1-allyl-cyclohexanecarbonitrile; ozonizing 1-allyl-cyclohexanecarbonitrile to obtain 1-cyano-cyclohexaneacetaldehyde; acetalizing 1-cyano-cyclohexaneacetaldehyde with a suitable acetalizing agent to give the corresponding acetal and converting the latter into gabapentin.

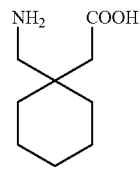

(1)

12 Claims, No Drawings

PROCESS FOR PREPARING GABAPENTIN

The present invention relates to a new process for the preparation of gabapentin. Gabapentin, 1-(aminomethyl)-cyclohexaneacetic acid (The Merck Index, XII Ed. page 733, n° 4343), is a known drug with anti-epileptic and anticonvulsant activity described for the first time in the U.S. Pat. No. 4,024,175 (Warner-Lambert).

U.S. Pat. No. 4,024,175 describes at least three methods of preparing gabapentin from cyclohexyl-1,1-diacetic acid. Each of these methods results in the formation of gabapentin hydrochloride salt, which may be converted to the corresponding acid by treatment with a basic ion exchanger and then crystallized from a solvent such as ethanol/ether.

In the literature several other processes and intermediates for the preparation of gabapentin are reported, see for example the U.S. Pat. Nos. 5,068,413, 5,091,567, 5,132,451, 5,319,135, 5,362,883, 5,693,845, 4,958,044, 4,956,473, 5,130,455, 5,095,148, 5,136,091 and 5,149,870.

Most of the above methods foresee a final step of gabapentin purification that consists in the treatment of an aqueous solution of a gabapentin salt (generally hydrochloride) through a weak basic ionic exchange resin, the complete evaporation of water from the aqueous gabapentin solution eluted from the resin and the crystallization from an alcoholic solvent, generally methanol or methanol/isopropanol or ethanol/ether mixtures.

WO 98/28255 (Teva) discloses a process for the preparation of gabapentin from the corresponding hydrochloride, which comprises the purification of gabapentin hydrochloride from the inorganic salts deriving from the synthesis by dissolving gabapentin hydrochloride in organic solvents wherein the inorganic salts are insoluble, filtration and optional evaporation of the solvent; treatment of a gabapentin hydrochloride solution with an amine in a solvent so as to precipitate gabapentin form III and final crystallization to obtain gabapentin form II.

WO 00/58268 (Bioindustria Laboratorio Italiano Medicinali) describes the separation of the inorganic salts from gabapentin is carried out by diafiltration.

WO 02/34709 (Zambon) describes a single process for the purification of gabapentin hydrochloride from the inorganic salts and for its conversion in gabapentin by treatment of an aqueous gabapentin hydrochloride solution through a strong cationic resin.

We have now found an advantageous, efficient and economical alternative process for the preparation of gabapentin of formula 1

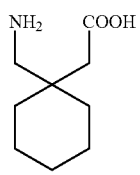

1 which progresses from cheap staring materials and reagents and would be industrially feasible with modest amount of solid wastes.

Said process, which represents a first object of the present invention, comprises:

Step 1

(i) converting 1-allyl-cyclohexanecarboxaldehyde of formula 2

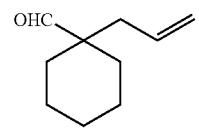

2 into 1-allyl-cyclohexanecarbonitrile of formula 3

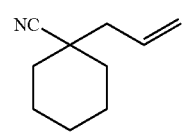

3

(ii) ozonizing the compound of formula 3 to obtain 1-cyano-cyclohexaneacetaldehyde of formula 4

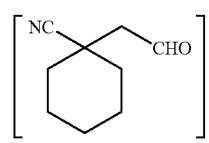

4 wherein the square brackets denote that, only if desired, the compound of formula 4 is isolated from the reaction mixture;

(iii) acetalizing the compound of formula 4 with a suitable acetalizing agent selected from the group consisting of $C_1$-$C_4$ alkanols and $C_2$-$C_4$-alkane diols, to give the corresponding acetal of formula 5

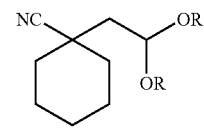

5 wherein each R is $C_1$-$C_4$ alkyl, or both R, taken together, form an ethylene bridge optionally substituted with one or two methyl groups or a propylene bridge optionally substituted with a methyl group; and Step 2 converting a compound of formula 5 into gabapentin of formula 1.

According to the present invention, the term "$C_1$-$C_4$-alkyl" means, unless otherwise specified, methyl, ethyl, 1-propyl, isopropyl, 1-butyl, sec-butyl or t-butyl, methyl and ethyl being preferred.

According to the present invention, the acetalizing agent is selected from the group consisting of $C_1$-$C_4$-alkanols such as, e.g., methanol, ethanol, 1-propanol, 2-propanol, 1-butanol, 2-methyl-1-propanol, 2-butanol and 2-methyl-2-propanol; and $C_2$-$C_4$-alkane diols such as, e.g., 1,2-ethane diol, 1,2- propane diol, 1,3-propane diol and 2,3-butane diol, with 1,2-ethane diol (ethylene glycol) being preferred.

In a preferred embodiment, the compound of formula 4 is prepared in situ from the compound of formula 3 according to Step 1 (ii) and without its isolation is used for the subsequent reaction Step 1 (iii). However, the compound of formula 4 can, of course, also be isolated before using it for the reaction according to Step 1 (iii).

In another preferred embodiment of the present invention, the compound of formula 5 obtained under Step 1 (iii) is 1-(1,3-dioxolan-2-ylmethyl)cyclohexanecarbonitrile of formula 5a

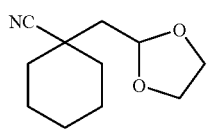

5a

The conversion of a compound of formula 5 into gabapentin of formula 1 according to Step 2 may be carried out following different procedures.

In a first aspect, Step 2 comprises:

(iv) reducing a compound of formula 5 as defined above to afford a compound of formula 6

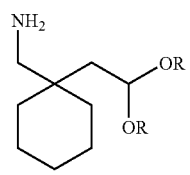

6 wherein R is as defined above;

(v) contacting a compound of formula 6 with ozone as oxidizing agent, in the presence of an acid HA selected from hydrochloric acid, phosphoric acid, formic acid and trifluoroacetic acid, to give a compound of formula 7

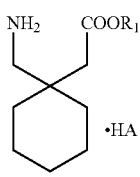

7 wherein $R_1$ is $C_1$-$C_4$ alkyl, β-hydroxy-ethyl optionally substituted with one or two methyl groups or γ-hydroxy-propyl optionally substituted with a methyl group, and HA is as defined above;

(vi) hydrolyzing a compound of formula 7 into the corresponding acid salt of gabapentin of formula 1 and, if desired, (vii) converting the acid salt of gabapentin of formula 1 into gabapentin of formula 1; or alternatively Step 2 comprises:

(iv') oxidizing a compound of formula 5 with ozone as oxidizing agent, to obtain a compound of formula 8

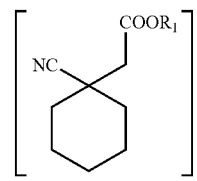

8 wherein $R_1$ is $C_1$-$C_4$ alkyl, β-hydroxy-ethyl optionally substituted with one or two methyl groups or γ-hydroxy-propyl optionally substituted with a methyl group, and the square brackets denote that, only if desired, the compound of formula 8 is isolated from the reaction mixture;

(v') hydrolysing a compound of formula 8 to obtain 1-cyano-cyclohexaneacetic acid and reducing the latter into gabapentin of formula 1; or, alternatively, (vi') reducing a compound of formula 8 in the presence of an acid HA selected from hydrochloric acid, phosphoric acid, formic acid and trifluoroacetic acid, to give a compound of formula 7 as defined above and hydrolysing a compound of formula 7 into the corresponding acid salt of gabapentin of formula 1 and, if desired, converting the acid salt of gabapentin of formula 1 into gabapentin of formula 1.

In a particular aspect, a compound of formula 8 wherein $R_1$ is β-hydroxy-ethyl optionally substituted with one or two methyl groups or γ-hydroxy-propyl optionally substituted with a methyl group is converted into a compound of formula 8 wherein $R_1$ is $C_1$-$C_4$ alkyl before undergoing the subsequent reaction Step 2 (v') as described above.

In a preferred embodiment, the compound of formula 8 is prepared in situ from the compound of formula 5 according to Step 2 (iv') and without its isolation is used for the subsequent reaction Step 2 (v'). However, the compound of formula 8 can, of course, also be isolated before using it for the reaction according to Step 2 (v').

As told above, an acid HA selected from the group consisting of hydrochloric acid, phosphoric acid, formic acid and trifluoroacetic acid, trifluoroacetic acid being the preferred one, especially for preventing lactamization when the amino group is expressed.

It is a another object of the present invention a process for the preparation of gabapentin of formula 1 as defined above, which comprises from reaction Step 2 (iv) to reaction Step 2 (vii) as defined above.

It is still another object of the present invention a process for the preparation of gabapentin of formula 1 as defined above, which comprises from reaction Step 2 (iv') to reaction Step 2 (vi') as defined above.

A process for the preparation of an intermediate compound of formula 5 as defined above, which comprises from reaction Step 1 (i) to reaction Step 1 (iii) as defined above, is also encompassed by the present invention.

A process for the preparation of an intermediate compound of formula 6, which comprises from reaction Step 1 (i) to reaction Step 2 (iv) as defined above, is moreover encompassed by the present invention.

The intermediate compounds of formula 5 and 6, wherein each R is other than ethyl, are novel compounds and therefore represent a further object of the present invention. The compounds of formula 5 and formula 6, wherein each R is ethyl are known compounds and can be prepared, for example, according to the procedure described in the EXAMPLES 1 and 2 of U.S. Pat. No. 4,515,960.

The present invention also provides to novel intermediate compounds of formula 5

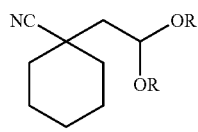

5 wherein each residue R is methyl, $C_3$-$C_4$ alkyl, or both residues R, taken together, form an ethylene bridge optionally substituted with one or two methyl groups or a propylene bridge optionally substituted with a methyl group. In a compound of formula 5, both R residues are, preferably, taken together to form an unsubstituted ethylene bridge.

The present invention additionally provides to novel intermediate compounds of formula 6

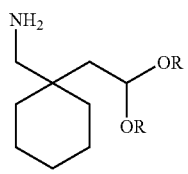

6 wherein each R residue is methyl, $C_3$-$C_4$ alkyl, or both residues R, taken together, form an ethylene bridge optionally substituted with one or two methyl groups or a propylene bridge optionally substituted with a methyl group. In a compound of formula 6, both R residues are, preferably, taken together to form an unsubstituted ethylene bridge.

A process for the preparation of an intermediate compound of formula 8 as defined above, which comprises from reaction Step 1 (i) to reaction Step 2 (v') as defined above, is also encompassed by the present invention.

The preparation of the starting compound of formula 2 can be carried out following known methods; for example, following the procedure described in *JACS* 1959, 81, 3379-3383, or U.S. Pat. No. 2,947,786, by mixing cyclohexanecarboxaldehyde with allyl alcohol in the presence of p-toluenesulfonic acid, at a temperature of 100-170° C., for a period of time of 15 h, in the presence of an organic solvent such as, for example, benzene or toluene. Cyclohexanecarboxaldehyde and allyl alcohol (also known as propene-1-ol or 2-propenyl alcohol) are commercially available products or may be prepared following procedures well known in the art.

The preparation of the compound of formula 3 under reaction Step 1 (i) can be carried out according to known procedures, for example following the procedure disclosed in *Synthesis* 1979, 112-114, by mixing under stirring a solution of the compound of formula 2 and hydroxylamine hydrochloride in 95-97% formic acid, at reflux, until complete conversion. Alternatively, the compound of formula 3 can be prepared according to the procedure described in, for example,

*Organic Letters* 2004, Vol. 6, No. 4, 501-3, which comprises reacting a compound of formula 9

9 wherein X is Br or Cl with Br—$CH_2$—CH=$CH_2$.

The preparation of the compound of formula 4 under reaction Step 1 (ii) can be carried out by bubbling an ozone-oxygen mixture into the solution of the compound of formula 3 in a suitable solvent such as, for example, methanol, operating at a temperature of from −40° C. to 60° C., preferably from −10° C. to 20° C., for a time enough to obtain a complete conversion of the compound of formula 4, and then reducing the peroxide intermediates with conventional methods, for example addition of dimethylsulfide to the reaction mixture or preferably catalytic hydrogenation of the reaction mixture. If desired, the compound of formula 4 can be isolated or, usually, it can be processed further to obtain a compound of formula 5. Advantageously, the preparation of the compound of formula 4 and its conversion to a compound of formula 5 can be carried out in a single reaction vessel without isolating the intermediate compound of formula 4. The compound of formula 4 can also be prepared according to the procedure described in *JACS* 1982, 104, 6649-50, which comprises reacting cyclohexane acetaldehyde in the presence of ethyl-aluminium dichloride with tert-butyl isocyanide.

The acetalization of the compound of formula 4 under reaction Step 1 (iii) can be carried out following conventional procedures well known to a person skilled in the art. For example, the acetalization of the compound of formula 4 with a $C_1$-$C_4$ alkanol to afford a compound of formula 5 wherein each R is a $C_1$-$C_4$ alkyl can be carried out in methanol as a solvent, in the presence of a suitable catalyst such as, for example, methanesulfonic acid, operating at room temperature and using methyl orthoformate as dehydrating agent. For example, the acetalization of the compound of formula 4 with a $C_2$-$C_4$-alkane diol to afford a compound of formula 5 wherein both R, taken together, form an ethylene bridge optionally substituted with one or two methyl groups or a propylene bridge optionally substituted with a methyl group can be carried out in the presence of a suitable solvent such as, e.g., cyclohexane and methanesulfonic acid, operating under reflux, with the aid of a Dean-Stark tube.

The reduction of a compound of formula 5 under reaction Step 2 (iv) to give a compound of formula 6 can be carried out according to conventional techniques. For example, said reduction can be performed following the method described in the U.S. Pat. No. 4,620,012, by contacting a compound of formula 5 with a suitable reducing agent such as, for example, $LiAl_4$, in an aprotic solvent, such as, for example, diethyl ether or tetrahydrofuran (THF), at a temperature of from 0° C. to 80° C., preferably from 20° C. to 60° C., for a time of about 2 h, on 100 mmol scale, counted from the onset of the dropping of 5 into the mixture of $LiAlH_4$ in diethyl ether. As an alternative, the preparation of a compound of formula 6 can be carried out by catalytic hydrogenation of a compound of formula 5, following typical procedures for the nitrile reduction, such as those reported in *Heterocycles* 2005, 66, 385-403.

The oxidation of a compound of formula 6 under reaction Step 2 (v) to give a compound of formula 7 can be carried out in an aprotic solvent such as, e.g., CHCl$_3$, CH$_3$OH, CH$_2$Cl$_2$, butylacetate or ethylacetate, after salification of the compound of formula 6 with an enough strong acid HA selected from hydrochloric acid, phosphoric acid, formic acid and trifluoroacetic acid, preferably trifluoroacetic acid, at a temperature of from −20° C. to 50° C., preferably from −10° C. to 10° C.

The hydrolysis of a compound of formula 7 into the acid salt of gabapentin of formula 1 under reaction Step 2 (vi) can be carried out by adapting the procedure described in *Chem. Pharm Bull*. 1976, 24, 1050-1058.

The conversion of an acid salt of gabapentin of formula 1 into the corresponding free amino acid under reaction Step 2 (vii) can be carried out according to procedures well known in the art. For example, when the acid salt of gabapentin is the hydrochloride salt, said salt can be converted into gabapentin by the treatment with a basic ion exchanger and then crystallized from a solvent such as ethanol/ether according to the method described in the U.S. Pat. No. 4,024,175, or by treatment with a strong cationic resin according to the procedure described in the international patent application WO 02/34709.

The oxidation of a compound of formula 5 into a compound of formula 8 under reaction Step 2 (iv') can be carried out following the procedure for converting cyclic and acyclic acetals to esters by ozonolysis as described in the Canadian patent No. 962,264. For example, the oxidation of a compound of formula 5 into a compound of formula 8 can be carried out by bubbling an ozone-oxygen mixture through the solution of compound of formula 5, in a solvent, such as, for example, butyl acetate, ethyl acetate or methanol, at a temperature of from −10° C. to 30° C., preferably from 0° C. to 15° C.

The conversion of a compound of formula 8 wherein R$_1$ is β-hydroxy-ethyl optionally substituted with one or two methyl groups or γ-hydroxy-propyl optionally substituted with a methyl group, into the corresponding compound of formula 8 wherein R$_1$ is a C$_1$-C$_4$ alkyl before undergoing reaction Step 2 (v'), can be carried out according to transesterification procedures known in the art, for example following the method described in *Tetrahedron* 1993, 49, 10501.

The hydrolysis of a compound of formula 8 into 1-cyano-cyclohexaneacetic acid under reaction Step 2 (v') can be carried out according to conventional procedures well known to a person skilled in the art. The subsequent reduction of 1-cyano-cyclohexaneacetic acid can be carried out, for example, by catalytic hydrogenation, in the presence of a suitable catalyst according to the method reported in *Chemicke Listy pro Vedu a Prumysl.* 1953, 47, 1241-3, or following the procedure described in the European patent No. 414,262.

Alternatively, the reduction of a compound of formula 8 into a compound of formula 7 under reaction Step 2 (vi') can be carried out by catalytic hydrogenation under acid conditions, in the presence of a suitable catalyst, according to the procedure reported in *Heterocycles* 2005, 66, 385-403. The subsequent hydrolysis of a compound of formula 7 into the acid salt of gabapentin and the following conversion to gabapentin of formula can be carried out following the procedure already described above.

The following examples illustrate but do not limit the present invention.

EXAMPLE 1

Preparation of 1-allyl-cyclohexanecarboxaldehyde (compound of formula 2)

A mixture of cyclohexanecarboxaldehyde ((10 mL, 0.825 mol), allyl alcohol (60 mL, 98% purity, 0.882 mol), benzene (15 mL), and p-toluenesulfonic acid monohydrate (0.120 g, 0.63 mmol) was heated from 130° C. to 180° C. in an oil bath, under a Vigreaux distillation column, topped by a Dean-Stark trap. After 15 hour no more water was added over the 15 mL collected in the trap, and the reaction was judged completed. Subsequent distillation of the reaction crude gave 98 g (78% yield) of 1-allyl-cyclohexanecarboxaldehyde as a colourless liquid (b.p. 69-71° C./5 mm Hg).

$^1$H-NMR (200 MHz, CDCl$_3$): δ 1.22-1.65 (10H, m, —(CH$_2$)$_5$—); 2.17 (2H, m, —CH$_2$—CH=); 4.96-5.07 (2H, m, CH=CH$_2$); 5.55-5.76 (1H, m, CH=CH$_2$); 9.44 (1H, s, CHO).

$^{13}$C-NMR (200 MHz, CDCl$_3$): δ 22.41 (CH$_2$); 25.61 (CH$_2$); 30.73 (CH$_2$); 40.72 (CH$_2$); 49.56 (C$^{IV}$); 118.21 (CH$_2$=); 132.64 (CH=); 206.70 (CHO).

IR (film): 1730 cm$^{-1}$ (C=O); 2861 cm$^{-1}$ (CHO).

MS (EI 70 eV): m/z 152 (3%, M$^+$); 137 (5); 134 (6); 123 (18); 110 (37); 108 (8); 97 (29); 81 (100); 55 (19); 41 (28).

EXAMPLE 2

Preparation of 1-allyl-cyclohexanecarbonitrile (compound of formula 3)

Compound 2 (125 g, 0.824 mmol) and hydroxylamine hydrochloride (66 g, 0.948 mol) were diluted with 95-97% formic acid (200 mL, 6.43 mol). A strong exothermic reaction occurred, after which the solution was maintained at refluxed by heating for a total time of 0.5 h. The reaction mixture was then allowed to cool. It was concentrated, diluted with ice-water (20 mL), neutralized with NaOH 5% and extracted with CH$_2$Cl$_2$ (3×40 mL). The organic extracts were collected and evaporated under vacuum. The crude product was purified by distillation (b.p. 88° C./5 mmHg) giving 99.5 g of 1-allyl-cyclohexanecarbonitrile as a colourless liquid (yield 81%).

$^1$H-NMR (200 MHz, CDCl$_3$): δ 1.11-1.955 (10H, m, —(CH$_2$)$_5$—); 2.25 (2H, d, J=7.3 Hz, —CH$_2$—CH=); 5.08-5.19 (2H, m, CH=CH$_2$); 5.75-5.96 (1H, m, CH=CH$_2$).

$^{13}$C-NMR (200 MHz, CDCl$_3$): δ 22.94 (CH$_2$); 25.26 (CH$_2$); 35.31 (CH$_2$); 38.79 (C$^{IV}$); 44.54 (CH$_2$); 119.50 (CH$_2$=); 123.19 (CN); 131.92 (CH=).

IR (film): 2231 cm$^{-1}$ (CN).

m/z (EI): m/z 149 (100%, M$^+$); 134 (25); 121 (34); 108 (58); 94 (7); 92 (11); 81 (93); 67 (33); 53 (16); 41 (43).

EXAMPLE 3

Preparation of 1-(2,2-dimethoxyethyl)-cyclohexanecarbonitrile (compound of formula 5, wherein each R is CH$_3$)

Compound 3 (45 g, 0.302 mol) was dissolved in methanol (60 mL) and thermostatted at −10° C. in a cylindrical flask, under magnetic stirring. The effluent stream of O$_3$/O$_2$ from an ozone generator (40 mmol/h of O$_3$) was bubbled into the solution until the starting material was all converted (9.5 h; GC monitoring). Next dimethyl sulphide (22.5 mL) was carefully added in such a way that temperature was never above 25° C. After 1 h methyl orthoformate (50 mL) and few drops of methanesulphonic acid were introduced into the reaction mixture. This was left under stirring at room temperature overnight; afterwards it was neutralized with LiH. The solvent was evaporated and the concentrate was distilled affording 50 g of 1-(2,2-dimethoxyethyl)-cyclohexanecarbonitrile (84% yield) as a colourless liquid (b.p. 115° C./1.4 mm Hg).

$^1$H NMR (CDCl$_3$, 200 MHz): δ 1.0-2.02 (10H, m, C$_6$H$_{10}$), 1.82 [2H, d, J=5.6 Hz, CH$_2$CH(OCH$_3$)$_2$], 3.36 (6H, s, 2×OCH$_3$), 4.64 [1H, t, J=5.6 Hz, CH(OCH$_3$)$_2$].

IR (film): 2232 (CN) cm$^{-1}$.

m/z (EI): 196 (1%, M$^+$−1), 166 (43), 108 (13), 81 (13), 75 (100).

EXAMPLE 4

Preparation of 1-(1,3-dioxolan-2-ylmethyl)cyclohexanecarbonitrile (compound of formula 5 wherein both R, taken together, form an ethylene bridge)

Compound 3 (206 g, 1,383 mol) was dispersed in ethylen glycol/t-butanol (400 mL/150 mL). The ensuing emulsion was thermostatted at 20° C., afterwards the effluent stream of O$_3$/O$_2$ from an ozone generator (30 mmol/h of O$_3$) was bubbled into it, under mechanical stirring, until the starting material was all converted (GC monitoring). Next dimethyl sulphide (120 mL) was carefully added in such a way that temperature was never above 25° C. After 1 h the solution was concentrated under vacuum and gentle heating to remove all the t-butanol. A further amount of ethylen glycol (100 mL), cyclohexane (100 mL) and methanesulphonic acid (1 mL) were then added into the residue. This was heated in an oil bath, under a Vigreaux distillation column, topped by a Dean-Stark trap, until no more water separated. The reaction mixture was subsequently diluted with water (1.5 L) and extracted with CH$_2$Cl$_2$ (6×100 mL). The organic phases were collected and evaporated. The resulting concentrate was distilled affording 202 g of 1-(1,3-dioxolan-2-yl-methyl)-cyclohexanecarbonitrile (75% yield) as a colourless liquid (b.p. 128° C./1.1 mm Hg).

$^1$H NMR (CDCl$_3$, 200 MHz): δ 1.0-2.18 (10H, m, C$_6$H$_{10}$), 1.92 [2H, d, J=4.8 Hz, CH$_2$CH(OCH$_2$)$_2$], 3.96 (4H, s, OCH$_2$CH$_2$O), 5.11 [1H, t, J=4.8 Hz, CH(OCH$_2$)$_2$].

IR (film): 2232 (CN) cm$^{-1}$.

m/z (EI): 194 (1%, M$^+$−1), 73 (100).

EXAMPLE 5

Preparation of 1-aminomethyl-1-(2,2-dimethoxyethyl)cyclohexane (compound of formula 6 wherein each R is CH$_3$)

In a 500 mL round bottomed flask, equipped by condenser, CaCl$_2$ tube and dropping funnel, were added LiAlH$_4$ (9.5 g, 250 mmol) and anhydrous ethyl ether (180 mL). Under vigorous stirring, a solution of 1-(2,2-dimethoxyethyl)-cyclohexanecarbonitrile (19.7 g, 100 mmol) in anhydrous ethyl ether (40 mL) was dropped in at a rate such as to maintain a gentle reflux. When addition was completed, the reflux was continued for further 2 h by mild heating. Careful extinction of residual LiAlH$_4$ with isopropanol (0.8 mol, 60 mL) and brine (50 mL) gave a white precipitate of aluminium hydroxide. The mixture was filtered and the cake washed with ether. Filtrate and ethereal washings were collected and concentrated under vacuum, giving 19.1 g of 1-aminomethyl-1-(2,2-dimethoxyethyl)cyclohexane as a colourless oil (95% yield).

$^1$H NMR (CDCl$_3$, 200 MHz): δ 1.1-1.5 (10H, m, C$_6$H$_{10}$), 1.59 [2H, d, J=5.1 Hz, CH$_2$CH(OCH$_3$)$_2$], 2.52 (2H, s, CH$_2$NH$_2$), 3.30 (6H, s, 2×OCH$_3$), 4.42 [1H, t, J=5.1 Hz, CH(OCH$_3$)$_2$].

IR (film): 3401 (NH$_2$) cm$^{-1}$.

m/z (EI): 186 (12%, M$^+$−15), 140 (60), 138 (45), 136 (100), 122 (28), 111 (56), 108 (98), 75 (62).

EXAMPLE 6

Preparation of 1-aminomethyl-1-(1,3-dioxolan-2-ylmethyl)cyclohexane (compound formula 6, wherein both R, taken together, form an ethylene bridge)

In a 250 mL round bottomed flask, equipped by condenser, CaCl$_2$ tube and dropping funnel, were added LiAlH$_4$ (4.75 g, 125 mmol) and anhydrous ethyl ether (90 mL). Under vigorous stirring, a solution of 1-(1,3-dioxolan-2-ylmethyl)cyclohexanecarbonitrile (9.75 g, 50 mmol) in anhydrous ethyl ether (20 mL) was dropped in at a rate such as to maintain a gentle reflux. When addition was completed, the stirring was continued for further 2 h at room temperature. Careful extinction of residual LiAlH$_4$ with isopropanol (0.45 mol, 35 mL) and brine (20 mL) gave a white precipitate of aluminium hydroxide. The mixture was filtered and the cake washed with ether. Filtrate and ethereal washings were collected and concentrated under vacuum, giving 8.5 g of 1-aminomethyl-1-(1,3-dioxolan-2-ylmethyl)cyclohexane as a colourless oil (85% yield).

$^1$H NMR (CDCl$_3$, 200 MHz): δ 1.10-1.60 (10H, m, C$_6$H$_{10}$), 1.71 [2H, d, J=4.7 Hz, CH$_2$CH(OCH$_2$)$_2$], 2.62 (2H, s, CH$_2$NH$_2$), 3.70-4.10 (4H, m, CH(OCH$_2$)$_2$), 4.89 [1H, t, J=4.7 Hz, CH(OCH$_2$)$_2$].

IR (film): 3394 (NH$_2$) cm$^{-1}$.

m/z (EI): 200 (<1%, M$^+$+1), 170 (3), 136 (10), 127 (7), 122 (56), 108 (22), 75 (100).

EXAMPLE 7

Preparation of 1-aminomethyl-1-(2,2-diethoxyethyl)cyclohexane (compound of formula 6, wherein each R is ethyl) (U.S. Pat. No. 4,515,960)

Anhydrous diethylamine, 51.7 mL (0.5 mol) was added dropwise to 312.5 ml (0.5 mol) of a 15% solution of n-butyl-lithium in hexane at −10° C. under an inert gas blanket. The batch was stirred for 10 minutes and then cooled to −70° C. Within 30 minutes, 54.6 g of cyclohexanecarbonitrile were added dropwise, after a further 30 minutes 98.5 g of bromoacetaldehydediethylacetal were added within 1 hour, and the batch was maintained for 24 hours at low temperature. Subsequently, it was warmed to room temperature, given onto 100 g of ice, extracted twice with 500 ml of ethyl acetate, the organic phase was dried over sodium sulphate, concentrated in vacuum, and the residue was subjected to vacuum distillation. Yield: 90 g (80% of th.) b.p. 78-79° C. at 8 mm Hg.

90 g of or 1-(2-diethoxyethyl)-cyclohexanecarbonitrile were dissolved in 1 l of ethanol, and 60 g of sodium were added. After dissolution of the metal, 100 ml of water were added, and the solvent was substantially removed in vacuum. 300 ml of water were added to the residue, and it was extracted three times with 200 ml of ether. The ethereal phase was dried over sodium sulphate, concentrated, and distilled in vacuum. Yield 93 g (abt. 90% of th.) b.p. 69-72° C. at 8 mm Hg.

EXAMPLE 8

Preparation of hydroxyethyl (1-cyano-cyclohexyl)acetate (compound of formula 8, wherein R$_1$ is hydroxyethyl)

1-(1,3-dioxolan-2-ylmethyl)cyclohexanecarbonitrile (45 g, 0.231 mol) was solubilized in butyl acetate (60 mL). The solution was thermostatted at 25° C., after which the bubbling of the effluent stream of $O_3/O_2$ from an ozone generator (15 mmol/h of $O_3$) was started. When all the starting material was converted (GC monitoring), the ozonation was interrupted leaving only the $O_2$ flowing so to chase the residual $O_3$. Next dimethyl sulphide (20 mL) was carefully added in such a way that temperature was never above 35° C. After 2 h the solution was concentrated under vacuum, giving 62.32 g of a crude containing aprox. 70% (GC value) of hydroxyethyl (1-cyano-cyclohexyl)acetate. A small sample was further purified for characterisation by distilling out the volatile fraction, mainly dimethylsulfoxide.

$^1$H NMR (CDCl$_3$, 200 MHz): δ 1.00-2.20 (10H, m, C$_6$H$_{10}$), 2.61 (2H, s, CCH$_2$CO), 3.86 [2H, m, (CO)OCH$_2$CH$_2$O], 4.28 [2H, m, (CO)OCH$_2$CH$_2$O].

IR (film): 3458 (OH) cm$^{-1}$; 2235 (CN) cm$^{-1}$; 1740 (CO) cm$^{-1}$.

m/z (EI): 212 (<1%, M$^+$−1), 184 (6), 181 (18), 150 (73), 139 (20), 122 (37), 108 (83), 104 (58), 95 (58), 94 (63), 86 (38), 81 (100).

EXAMPLE 9

Preparation of methyl (1-cyano-cyclohexyl)acetate (compound of formula 8, wherein R$_1$ is methyl)

The crude hydroxyethyl (1-cyano-cyclohexyl)acetate, obtained from 1-(1,3-dioxolan-2-yl-methyl)cyclohexanecarbonitrile (45 g, 0.231 mol), following the procedure reported in example 8, was diluted with CH$_3$OH (250 mL) and charged with K$_2$CO$_3$ (13 g). The mixture was stirred for 1 h, filtered and the recovered filtrate neutralized with HCl 37%. Next it was diluted with water (500 mL) and extracted with CH$_2$Cl$_2$ (6×100 mL). The organic phases were collected and evaporated. The resulting concentrate was finally distilled affording 31 g of methyl (1-cyano-cyclohexyl)acetate (57% yield) as a colourless liquid (b.p. 115° C./1.2 mm Hg).

$^1$H NMR (CDCl$_3$, 200 MHz): δ 1.00-2.15 (10H, m, C$_6$H$_{10}$), 2.53 (2H, s, CCH$_2$CO), 3.68 [3H, s, (CO)OCH$_3$].

IR (film): 2235 (CN) cm$^{-1}$; 1742 (CO) cm$^{-1}$;

m/z (EI): 182 (<1%, M$^+$+1), 154 (6), 150 (18), 108 (98), 74 (58).

EXAMPLE 10

Preparation of 1-cyano-cyclohexaneacetic acid 1-(1,3-dioxolan-2-ylmethyl)cyclohexanecarbonitrile (10 g, 0.051 mol) was solubilized in butyl acetate (30 mL). The solution was thermostatted at 25° C., after which the bubbling of the effluent stream of $O_3/O_2$ from an ozone generator (15 mmol/h of $O_3$) was started. When all the starting material was converted (GC monitoring), the ozonation was interrupted leaving only the $O_2$ flowing so to chase the residual $O_3$. Next dimethyl sulphide (5 mL) was carefully added in such a way that temperature was never above 35° C. After 2 h the solution was concentrated under vacuum. The residue was then diluted with MTBE (40 mL) and H$_2$O (100 mL). After thermostattation at 0° C., it was slowly added a solution of NaOH$_{aq}$ (10 g, 0.250 mol) in H$_2$O (15 mL), under vigorous stirring, until turbidity disappearance. The aqueous phase was separated and then, always at 0° C., was carefully acidified with HCl$_{aq}$ 18%. The organic acid, which separated, was recovered by washing the suspension with CH$_2$Cl$_2$ (3×30 mL). The organic phases were collected and evaporated under vacuum at room temperature, affording 7.05 g (yield 82%) of the 1-cyano-cyclohexaneacetic acid (>90% pure, GC), as a white solid (m.p. 99-104° C.

$^1$H NMR (CDCl$_3$, 200 MHz): δ 1.00-2.23 (10H, m, C$_6$H$_{10}$), 2.62 (2H, s, CH$_2$COOH).

IR (film): 3457 (OH) cm$^{-1}$; 2234 (CN) cm$^{-1}$; 1702 (CO) cm$^{-1}$.

m/z (EI): 167 (<1%, M$^+$), 140 (6), 122 (11), 108 (100), 81 (25), 80 (26).

EXAMPLE 11

Preparation of Gabapentin•HCl 1-aminomethyl-1-(1,3-dioxolan-2-ylmethyl)cyclohexane (1 g, 5 mmol) was solubilized in ethyl acetate (4 mL). The solution was thermostatted at −5° C., and acidified with trifluoroacetic acid (0.420 mL, 5.5 mmol), after which the bubbling of the effluent stream of $O_3/O_2$ from an ozone generator (10 mmol/h of $O_3$) was started. When all the starting material was converted (about 1 h, GC monitoring), the ozonation was interrupted leaving only the $O_2$ flowing so to chase the residual $O_3$. Next the solution was concentrated under vacuum. The H-NMR-spectrum of the crude was consistent with the structure of hydroxyethyl [1-(aminomethyl)cyclohexyl]acetateHCl (compound of formula 7 wherein R$_1$ is hydroxyethyl) {$^1$H NMR (CDCl$_3$, 200 MHz): δ 1.20-1.70 (10H, m, C$_6$H$_{10}$), 2.60 (2H, s, CCH$_2$CO), 3.07 (2H, s, CH$_2$NH$_3^+$), 3.83 [2H, m, (CO)OCH$_2$CH$_2$O], 4.26 [2H, m, (CO)OCH$_2$CH$_2$O]}.

The unprocessed ester was then diluted in AcOH (2 mL) and HCl$_{H2O}$ 18% (2 mL), afterward the solution, thus obtained, was heated at reflux. Elapsed 2 h, the volatile compounds were evacuated under vacuum. The residue was charged with acetone (4 mL) and cooled at 0° C. to help the precipitation (the addition of some ethyl ether can facilitate the phenomenon) of the gabapentrin HCl. The solid was recovered by filtration and washed with cold acetone, giving 0.645 g of a white powder (m.p. 124-125° C., yield 62%.

an. el., found: C, 52.1; H, 8.8; N, 6.7; C$_9$H$_{18}$ClNO$_2$ required: 52.05; H, 8.73; N, 6.74.

$^1$H NMR (CDCl$_3$, 200 MHz): δ 1.00-2.20 (10H, m, C$_6$H$_{10}$), 2.61 (2H, s, CCH$_2$CO), 3.86 [2H, m, (CO)OCH$_2$CH$_2$O], 4.28 [2H, m, (CO)OCH$_2$CH$_2$O].

IR (film): 3387 (—NH$_3^+$) cm$^{-1}$; 1713 (C=O) cm$^{-1}$.

EXAMPLE 12

Preparation of gabapentin from 1-cyanocyclohexaneacetic acid (U.S. Pat. No. 5,362,883)

To a 500-mL Parr bomb was added 23.5 g (0.1 mol) of 1-cyanocyclohexaneacetic acid, 28% water wet; 16 g of 50% water wet Raney nickel #30, and a cooled (20° C.) methyl alcohol (160 mL) and 50% aqueous sodium hydroxide (8.8 g, 0.11 mol) solution. The reaction mixture was stirred at 22° C. to 25° C. for 21 hours at 180 pounds per square inch gauge (psig) hydrogen. After 21 hours, the hydrogen was vented and the reduced mixture was flushed with nitrogen.

The reaction mixture was pressure filtered over celite, washed with methyl alcohol (100 mL), and stripped to a volume of 50 mL at 35° C. on the rotary evaporator. Isopropyl alcohol (100 mL) was added followed by the dropwise addition of 6.6 g (0.11 mol) of acetic acid. The product solution was stripped on the rotary evaporator to a volume of 50 mL.

Tetrahydrofuran (125 mL) was added to the concentrated product solution, the solution cooled in an ice bath, suction filtered, and washed using 50 mL of tetrahydrofuran. The crude product cake is dried under vacuum at 45° C. for 16 hours.

The crude product was recrystallized from methyl alcohol, demineralized water, and isopopyl alcohol to yield 10.3 g of gabapentin as a crystalline white solid. The high-performance liquid chromatography (HPLC) results showed no organic impurities detected with a 97.2% weight/weight (w/w) purity.

The invention claimed is:

1. A process for the preparation of gabapentin of formula 1

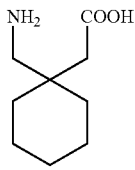

1 which comprises:

Step 1

(i) converting 1-allyl-cyclohexanecarboxaldehyde of formula 2

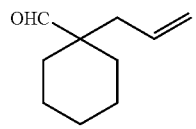

2 into 1-allyl-cyclohexanecarbonitrile of formula 3

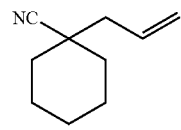

3

(ii) ozonizing the compound of formula 3 to obtain 1-cyano-cyclohexaneacetaldehyde of formula 4

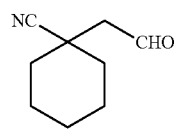

4

(iii) and acetalizing the compound of formula 4 with a suitable acetalizing agent selected from the group consisting of $C_1$-$C_4$ alkanols and $C_2$-$C_4$-alkane diols, to give the corresponding acetal of formula 5

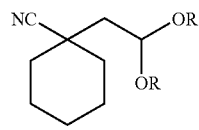

5 wherein each R is $C_1$-$C_4$ alkyl, or both R, taken together, form an ethylene bridge optionally substituted with one or two methyl groups or a propylene bridge optionally substituted with a methyl group; and Step 2 converting a compound of formula 5 into gabapentin of formula 1.

2. The process according to claim 1, wherein the compound of formula 4 is prepared in situ from the compound of formula 3 according to reaction Step 1 (ii) and without its isolation is used for the subsequent reaction Step 1 (iii).

3. The process according to claim 1, wherein the conversion of a compound of formula 5 into gabapentin of formula 1 of reaction Step 2 comprises:

(iv) reducing a compound of formula 5 as defined above to afford a compound of formula 6

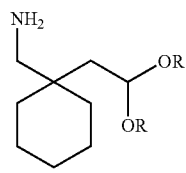

6 wherein R is as defined in claim 1;

(v) contacting a compound of formula 6 with ozone as oxidizing agent, in the presence of an acid HA selected from hydrochloric acid, phosphoric acid, formic acid and trifluoroacetic acid, to give a compound of formula 7

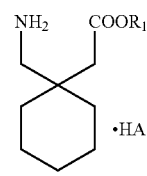

7 wherein $R_1$ is $C_1$-$C_4$ alkyl, β-hydroxy-ethyl optionally substituted with one or two methyl groups or γ-hydroxy-propyl optionally substituted with a methyl group, and HA is as defined above;

(vi) hydrolyzing a compound of formula 7 into the corresponding acid salt of gabapentin of formula 1 and, if desired, (vii) converting the acid salt of gabapentin of formula 1 into gabapentin of formula 1.

4. The process according to claim 1, wherein the conversion of a compound of formula 5 into gabapentin of formula 1 of reaction Step 2 comprises:

(iv') oxidizing a compound of formula 5 with ozone as oxidizing agent, to obtain a compound of formula 8

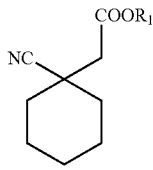
8 wherein $R_1$ is $C_1$-$C_4$ alkyl, β-hydroxy-ethyl optionally substituted with one or two methyl groups or γ-hydroxy-propyl optionally substituted with a methyl group, and the square brackets denote that, only if desired, the compound of formula 8 is isolated from the reaction mixture;

(v') hydrolysing a compound of formula 8 to obtain 1-cyano-cyclohexaneacetic acid and reducing the latter into gabapentin of formula 1; or, alternatively, (vi') reducing a compound of formula 8 in the presence of an acid HA selected from hydrochloric acid, phosphoric acid, formic acid and trifluoroacetic acid, to give a compound of formula 7

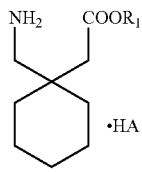
7 and hydrolysing a compound of formula 7 into the corresponding acid salt of gabapentin of formula 1 and, if desired, converting the acid salt of gabapentin of formula 1 into gabapentin of formula 1.

5. The process according to claim 4, in which a compound of formula 8 wherein $R_1$, is β-hydroxy-ethyl optionally substituted with one or two methyl groups or γ-hydroxy-propyl optionally substituted with a methyl group is converted into a compound of formula 8 wherein $R_1$ is $C_1$-$C_4$ alkyl, before undergoing the subsequent reaction Step 2 (V').

6. The process according to claim 4, wherein the compound of formula 8 is prepared in situ from the compound of formula 5 according to reaction Step 2 (iv') and without its isolation is used for the subsequent reaction Step 2 (v').

7. The process according to claim 1, wherein the acetalizing agent is selected from the group consisting of $C_1$-$C_4$-alkanols and $C_2$-$C_4$-alkane diols.

8. The process according to claim 1, wherein the acetalizing agent is ethylene glycol.

9. The process according to claim 3, wherein the acid HA is hydrochloric acid.

10. The process according to claim 3, wherein the acid HA is phosphoric acid.

11. The process according to claim 3, wherein the acid HA is formic acid.

12. The process according to claim 1, wherein the acid HA is trifluoroacetic acid.

* * * * *